United States Patent
An et al.

(10) Patent No.: US 9,726,656 B2
(45) Date of Patent: Aug. 8, 2017

(54) EXPERIMENT APPARATUS FOR ESTIMATING GROUND DEFORMATION DURING GAS HYDRATE RECOVERY

(71) Applicant: Korea Gas Corporation, Gyeonggi-do (KR)

(72) Inventors: Seung Hee An, Gyeonggi-do (KR); Young Soo Lee, Gyeonggi-do (KR); Young Mi Jang, Gyeonggi-do (KR); Young Ho Yang, Gyeonggi-do (KR)

(73) Assignee: Korea Gas Corporation, Gyeonggi-do (KR)

( * ) Notice: Subject to any disclaimer, the term of this patent is extended or adjusted under 35 U.S.C. 154(b) by 161 days.

(21) Appl. No.: 14/408,556

(22) PCT Filed: Aug. 13, 2013

(86) PCT No.: PCT/KR2013/007291
§ 371 (c)(1),
(2) Date: Dec. 16, 2014

(87) PCT Pub. No.: WO2015/005522
PCT Pub. Date: Jan. 15, 2015

(65) Prior Publication Data
US 2016/0238584 A1    Aug. 18, 2016

(30) Foreign Application Priority Data
Jul. 11, 2013   (KR) .................. 10-2013-0081303

(51) Int. Cl.
*G01N 3/12*     (2006.01)
*G01N 33/24*    (2006.01)
*G01V 99/00*    (2009.01)

(52) U.S. Cl.
CPC ............... *G01N 33/24* (2013.01); *G01N 3/12* (2013.01); *G01V 99/00* (2013.01)

(58) Field of Classification Search
CPC ...................................................... G01N 3/12
See application file for complete search history.

(56) References Cited

U.S. PATENT DOCUMENTS

| 5,417,824 A * | 5/1995 | Greenbaum | ............... C07C 1/00 204/157.15 |
|---|---|---|---|
| 2008/0088171 A1 | 4/2008 | Cheng | |
| 2014/0318557 A1* | 10/2014 | Bremer | ............. A24F 1/00 131/328 |

FOREIGN PATENT DOCUMENTS

| JP | 2006052395 A | 2/2006 |
|---|---|---|
| KR | 100786812 B1 | 12/2007 |

(Continued)

*Primary Examiner* — Laura Martin
*Assistant Examiner* — Alex Devito
(74) *Attorney, Agent, or Firm* — McDonnell Boehnen Hulbert & Berghoff LLP

(57) ABSTRACT

Disclosed herein is an experiment apparatus for estimating ground surface deformation during gas hydrate recovery. The experiment apparatus may include: a high-pressure cell having a space in which a sample containing gas hydrate is stored; a pressurizing member mounted to move in one direction in the high-pressure cell, and moved to pressurize the sample stored in the space, wherein the surface of the sample is observed along the longitudinal direction of the pressurizing member through the pressurizing member from outside; and a recovery member inserted into the sample so as to recover the gas hydrate contained in the sample to the outside.

10 Claims, 3 Drawing Sheets

(56) References Cited

FOREIGN PATENT DOCUMENTS

| KR | 1020090122812 A | 12/2009 |
|---|---|---|
| KR | 1020130037511 A | 4/2013 |

\* cited by examiner

[Fig. 1]
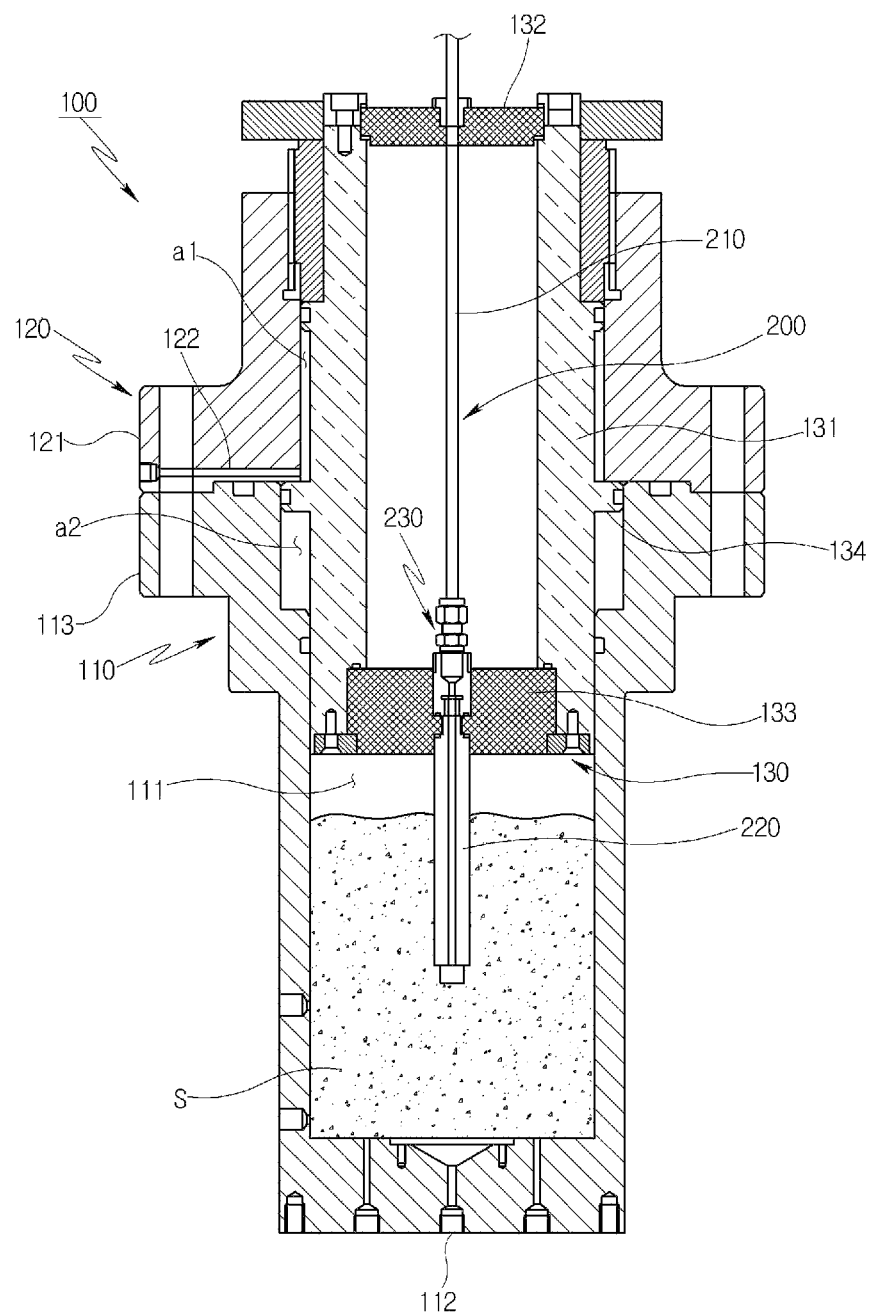

【Fig. 2】
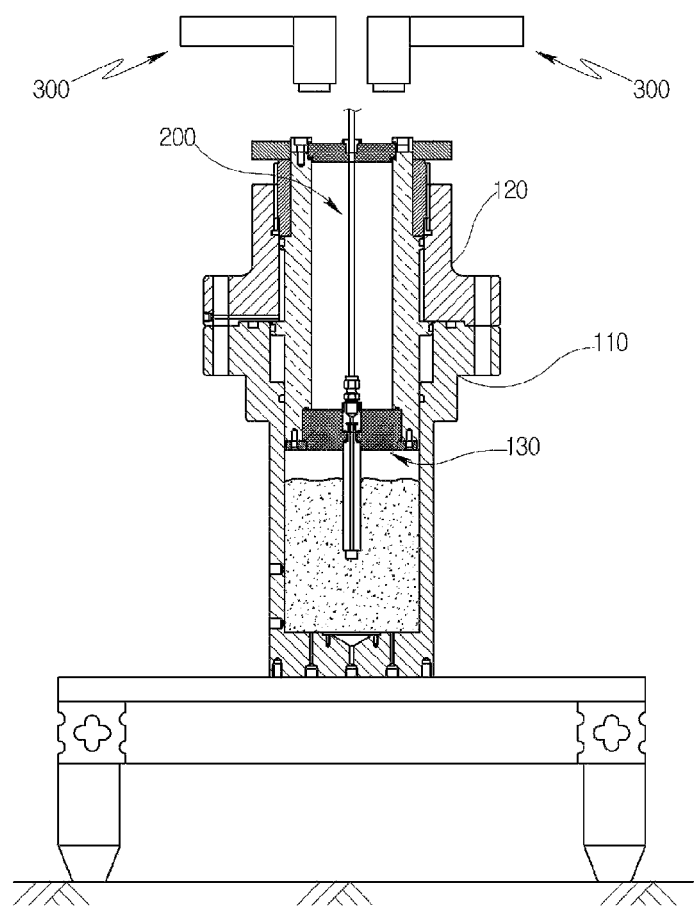

[Fig. 3]
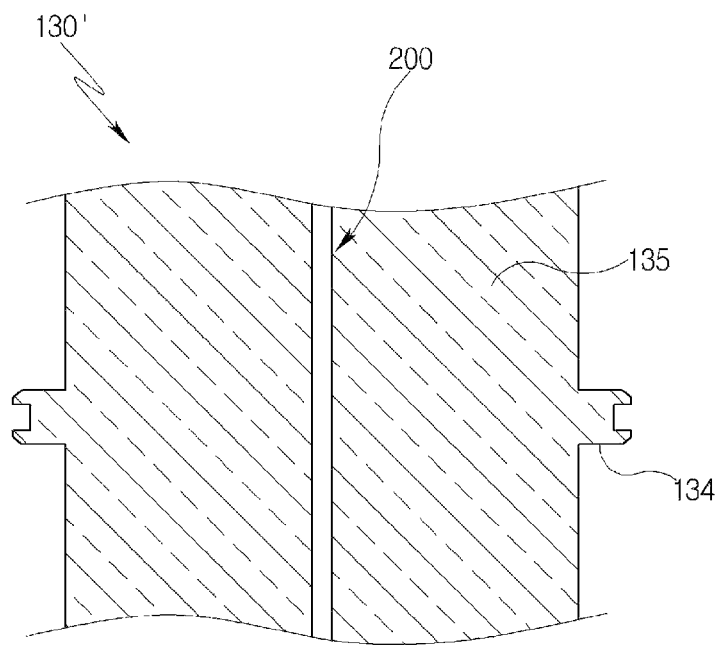
[Fig. 4]
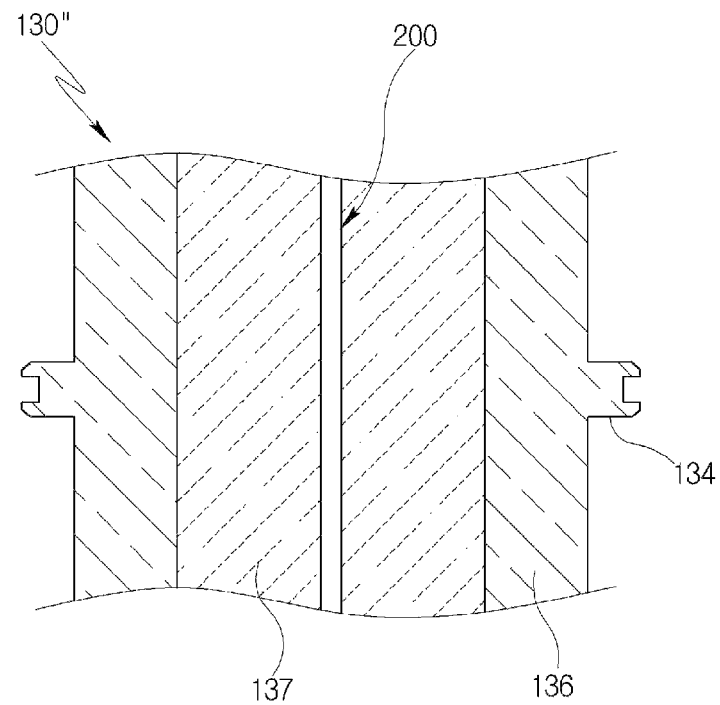

EXPERIMENT APPARATUS FOR ESTIMATING GROUND DEFORMATION DURING GAS HYDRATE RECOVERY

TECHNICAL FIELD

Exemplary embodiments of the present invention relate to an experiment apparatus for estimating ground surface deformation which may occur when gas hydrate is recovered.

BACKGROUND ART

Gas hydrate refers to a solid material which is formed when gas such as methane (CH4) is combined with water molecules (H2O) at a low temperature and high pressure of 0° C. and 26 atmospheres or 10° C. and 76 atmospheres. Gas hydrate is easily found in an area adjacent to an oil or natural gas reservoir and a coal bed in a frozen soil region or a low-temperature and high-pressure deep-sea sedimentary layer, or particularly a continental slope.

In order to utilize such gas hydrate as a resource, an advanced mining technology must be applied. When the pressure is lowered, gas hydrate is dissociated while releasing methane. Thus, it is difficult to mine gas hydrate in a solid state like coal. As a method for extracting only methane by dissociating hydrate, various methods are used, which includes a depressurization method, a thermal injection method, an inhibitor injection method, a replacement method and the like.

According to the depressurization method, a borehole is formed in a free gas layer adjacent to gas hydrate so as to reduce the pressure of the gas layer. As the pressure of the free gas layer is reduced, the hydrate of the gas hydrate layer is dissociated to generate gas.

According to the thermal injection method, steam or hot water is injected to increase the temperature of a gas hydrate reservoir. Then, hydrate is dissociated to generate gas. The thermal injection method may be considered when there is no free gas layer adjacent to gas hydrate.

According to the inhibitor injection method based on a technology which is used to prevent hydration in a cold region, an additive such as methanol or glycol is injected to change a dissociation condition. When only the inhibitor injection method is used, a significant effect may not be obtained. However, when a hydraulic fracturing method and the thermal injection method are used at the same time, the effect of the inhibitor injection method is expected to be improved. However, the inhibitor injection method has disadvantages in that environmental pollution is likely to occur and the economic efficiency thereof is low due to a high cost required for a solvent used therein.

According to the replacement method which is a method for altering the molecular structure of gas hydrate, captured methane is extracted by replacing methane within gas hydrate with another material. When the replacement method is used, methane may be produced without melting a gas hydrate layer.

In addition, the method for extracting only methane by dissociating hydrate includes a geothermal stimulation method which generates hot water using ground heat and injects the generated hot water, and a controlled oxidation method which dissociates hydrate through a catalytic oxidation reaction in a stratum.

The region abundant in gas hydrate may be roughly divided into two regions. In general, a large amount of gas hydrate is found in the permanently-frozen soil and the continental slopes in the deep ocean. Depending on where gas hydrate is buried, the difficulty level of recovery may differ. For example, when gas hydrate exists in the hard rocks, ground deformation or ground subsidence hardly occurs while the gas hydrate is recovered. However, when gas hydrate exists in unconsolidated strata in the sea, ground deformation or ground subsidence may occur while the gas hydrate is recovered. Thus, it is important to previously analyze a ground deformation characteristic on gas hydrate recovery through an experiment, and to estimate the extent to which the strata is deformed, based on the result obtained through the experiment. In the current technical field related to gas hydrate, there has been proposed only a method and apparatus for recovering gas hydrate or an apparatus for artificially generating gas hydrate as disclosed in Korean Patent Laid-open Publication No. 10-2009-0122812. However, an experiment apparatus capable of estimating ground deformation through observation during gas hydrate recovery has not yet been disclosed.

DISCLOSURE

Technical Problem

The present invention has been made in view of the above problems, and it is an object of the present invention to provide an experiment apparatus for estimating ground surface deformation during gas hydrate recovery, through observation for the surface of a sample stored therein.

Technical Solution

In accordance with one aspect of the present invention, an experiment apparatus may include: a high-pressure cell having a space in which a sample containing gas hydrate is stored; a pressurizing member mounted to move in one direction in the high-pressure cell, and moved to pressurize the sample stored in the space, wherein the surface of the sample is observed along the longitudinal direction of the pressurizing member through the pressurizing member from outside; and a recovery member inserted into the sample so as to recover the gas hydrate contained in the sample to the outside.

The pressurizing member may include: a hollow body mounted to move in one direction in the high-pressure cell; a first cap mounted at an opened end of the body; and a second cap mounted at the other opened end of the body so as to face the surface of the sample, and the first and second caps may be formed of a transparent material.

The second cap may be formed of a material containing quartz.

The surface of the pressurizing member, contacted with the surface of the sample through the movement of the pressurizing member, may be formed with one surface of the second cap.

The experiment apparatus may further include a photographing unit arranged to observe the surface of the sample through the first and second caps.

The pressurizing member may include an integrated body mounted to move in one direction in the high-pressure cell, and the body may be formed of a transparent material.

The body may be formed of a material containing quartz.

The experiment apparatus may further include a photographing unit arranged to observe the surface of the sample through the body.

The pressurizing unit may include: a hollow body arranged to move in one direction in the high-pressure cell; and a transparent member positioned in the body and formed of a transparent material.

The transparent member may be formed of a material containing quartz.

The experiment apparatus may further include a photographing unit arranged to observe the surface of the sample through the transparent member.

DESCRIPTION OF DRAWINGS

The above and other objects, features and other advantages of the present invention will be more clearly understood from the following detailed description taken in conjunction with the accompanying drawings, in which:

FIG. 1 is a cross-sectional view of an experiment apparatus according to an embodiment of the present invention;

FIG. 2 illustrates an arrangement state of cameras in the experiment apparatus according to the embodiment of the present invention; and FIGS. 3 and 4 illustrate other examples of a pressurizing member illustrated in FIG. 1.

BEST MODE FOR INVENTION

Hereafter, embodiments of the present invention will be described with reference to the accompanying drawings.

The present invention may include various modifications and various embodiments, and thus specific embodiments will be illustrated in the drawings and described in the detailed descriptions. However, the present invention is not limited to specific embodiments, and may include all of variations, equivalents, and substitutes within the scope of the present invention.

The terms including technical or scientific terms have the same meanings as the terms which are generally understood by those skilled in the art to which the present invention pertains, as long as they are differently defined. The terms defined in a generally used dictionary may be analyzed to have meanings which coincide with contextual meanings in the related art. As long as the terms are not clearly defined in this specification, the terms may not be analyzed as ideal or excessively formal meanings.

Furthermore, the following embodiments are provided for clear understanding of those skilled in the art, and the shapes and sizes of components in the drawings are exaggerated for clarity of description.

FIG. 1 is a cross-sectional view of an experiment apparatus according to an embodiment of the present invention. FIG. 2 illustrates an arrangement state of cameras in the experiment apparatus according to the embodiment of the present invention.

The experiment apparatus 1 for estimating ground surface deformation during gas hydrate recovery according to the embodiment of the present invention may include a high-pressure cell 100, a pressurizing member 130, and a recovery member 200. The high-pressure cell 100 may have a space 111 in which a sample S containing gas hydrate is stored. The pressurizing member 130 may be mounted to move in one direction in the high-pressure cell 100, and moved to pressurize the sample S stored in the space 111. The surface of the sample S may be observed along the longitudinal direction of the pressurizing member 130 from outside. The recovery member 200 may be inserted into the sample S so as to recover the gas hydrate contained in the sample S to the outside.

The high-pressure cell 100 included in the experiment apparatus 1 according to the embodiment of the present invention may function as a component of an apparatus for generating and recovering gas hydrate as well as the component of the experiment apparatus for estimating ground surface deformation during gas hydrate recovery. The high-pressure cell 100 which can be used for generating and recovering gas hydrate or observing ground surface deformation during a recovery process may include a first body 110 and a second body 120.

The first body 110 may be formed in a cylindrical shape, for example. The space 111 formed in the first body 110 may be opened upward, and the sample S for experiment may be stored in the space 111. The sample S may contain earth and sand such that ground surface deformation can be simulated. The sample S may already contain gas hydrate, or gas hydrate may be generated and contained in the sample S. The first body 110 may include a plurality of sensors (not illustrated) for measuring the pressure and temperature of the space 111. The first body 110 may have a first supply path 112 formed at one side thereof, for example, at the bottom thereof. Through the first supply path 112, water may be injected into the space 111. The first supply path 112 may be connected to a water tank (not illustrated) in which water is stored, and water supplied through the first supply path 112 may be supplied in a state where the water is cooled through a cooling device. For example, the supplied water may be cooled at a similar temperature to the internal temperature of the ground in an actual site. The first supply path 112 may be used as a supply path for methane gas which serves as a raw material for generating gas hydrate, as well as the supply path for water. For this structure, the first supply path 112 may be connected to a tank in which methane gas is stored. Furthermore, the first body 110 may have a first flange part 113 formed at the top thereof so as to be coupled to the second body 120 which will be described below.

The second body 120 may be coupled to the top of the first body 110. The second body 120 may be formed in a cylindrical shape, like the first body 110. The second body 120 may have a second flange part 121 formed at the bottom thereof, the second flange part 121 corresponding to the first flange part 113 of the first body 110. As the first and second flange parts 113 and 121 are stacked and coupled through a fastening member such as a bolt, the first and second bodies 110 and 120 may be coupled to each other. The second body 120 may also have a space formed therein. The internal space of the second body 120 may be opened upward, and communicate with the space 111 of the first body 110 in the downward direction.

The pressurizing member 130 may serve to pressurize the sample S stored in the space 111 of the first body 110. The pressurizing member 130 may be mounted to move upward and downward in the internal space of the second body 120. The pressurizing member 130 may include a hollow body 131, a first cap 132, and a second cap 133. The hollow body 131 may be mounted to move in one direction in the high-pressure cell 100. The first cap 131 may be mounted at the open top of the hollow body 131. The second cap 133 may be mounted at the open bottom of the hollow body 131 so as to face the surface of the sample S. The first body 110 may be formed in a cylindrical shape having a space formed therein. The second cap 133 may close the internal space of the body 131 with respect to the bottom of the body 131, and the bottom surface of the second cap 133 may form the bottom surface of the pressurizing member 130, which is contacted with the surface of the sample. In order that the sample S is stably pressurized by the pressurizing member 130 and the high-pressure state of the space 111 is maintained, there must be no clearance between the outer circumferential surface of the body 131 and the inner circumferential surface of the space 111. Thus, the bottom of the cylindrical body 131 may be formed to have the same outer diameter as the inner diameter of the space 111. At this time, since the internal space of the body 131 is sealed by the second cap 133, the space 111 may be sealed by the bottom surface of the pressurizing member 130 with respect to the top side.

The body 131 may have a protrusion 134 formed on the outer surface thereof, and the protrusion 134 may be formed along the circumferential direction of the body 131, while protruding in the diameter direction. The space between the inner circumferential surface of the second body 120 and the outer circumferential surface of the body 131 may be divided into an upper space a1 and a lower space a2 by the protrusion 134. The second body 120 may have a second supply path 122 communicating with the upper space a1, and the second supply path 122 may be connected to a pump (not illustrated) which supplies fluid at high pressure. Through the second supply path 122, a high-pressure fluid may be supplied to the upper space a1 so as to pressurize the body 131 downward. As the body 131 is pressurized downward, the pressurizing member 130 may be moved downward such that the sample S is pressurized by the second cap 133.

The recovery member 200 may be mounted in the pressurizing member 130 so as to vertically penetrate the pressurizing member 130, and recover fluid including gas hydrate or gas hydrate and water contained in the sample S to the outside through an end thereof, which is inserted into the sample S. The recovery member 200 may include a flow path pipe 210, an insertion part 220, and a connection member 230. The flow path pipe 210 may be fixed to the first cap 132 while passing through the first cap 132, and extended to the vicinity of the second cap 133 along the longitudinal direction of the body 131. The insertion part 220 may be extended downward such that a lower end thereof is positioned in the space 111 in a state where an upper end thereof is inserted and coupled to the bottom surface of the second cap 133 facing the sample S. The lower end of the flow path pipe 210 and the upper end of the insertion part 220 may be connected to each other by the connection member 230 which is inserted and fixed to the second cap 133. The insertion part 220 may have a flow path formed therein, the flow path communicating with the flow path of the flow path pipe 210. Thus, the gas hydrate or gas hydrate and water, recovered through the end of the insertion part 220, may be transferred to the outside through the flow path of the insertion part 220 and the flow path of the flow path pipe 210. The recovery member 200 may serve as a supply path for supplying a raw material into the sample S, in order to generate or dissociate gas hydrate. That is, the flow path pipe 210 may be connected to a raw material supply tank (not illustrated) for gas hydrate, and a raw material for generating or dissociating gas hydrate may be supplied into the sample S through the flow path of the flow path pipe 210 and the flow path of the intrusion part 220.

The experiment apparatus 1 according to the present embodiment may include the pressurizing member 130 through which an operator can observe surface deformation of the sample S, which occurs when the gas hydrate is recovered.

Specifically, when the pressurizing member 130 is formed with the above-described structure, the first and second caps 132 and 133 may be formed of a transparent material. Thus, the surface of the sample S in the space 111 may be observed through the first and second caps 132 and 133 from outside. In other words, the surface of the sample S in the space 111 may be observed along the longitudinal direction of the pressurizing member 130. At least the second cap 133 of the first and second caps 132 and 133 may be formed of a material containing quartz, for example. Alternatively, both of the first and second caps 132 and 133 may be formed of a material containing quartz. The high-pressure cell 100 may form a high pressure therein such that the sample S stored therein is placed under a similar condition to the ground of an actual site. The first and second bodies 110 and 120 forming the high-pressure cell 100 may be formed of stainless steel, for example, so as to endure the high pressure. Furthermore, the second cap 133 facing the space 111 also needs to endure high pressure, and the sample S needs to be observed through the second cap 133. Thus, as described above, the second cap 133 may be formed of a material containing quartz, for example.

Since the experiment apparatus 1 according to the embodiment of the present invention includes the pressurizing member 130 formed of a transparent material, an operator may observe the surface deformation of the sample S in the space 111 with the naked eye. Furthermore, a photographing unit may be used to precisely analyze the deformation of the sample S and to store the analysis results as data. The photographing unit may include a high-sensitivity camera 300 which can take an image. As illustrated in FIG. 2, the camera 300 may be arranged outside the high-pressure cell 100 so as to face the first cap 132, and take an image of the surface deformation of the sample S through the first and second caps 132 and 133. At this time, a plurality of cameras 300 may be arranged, and controlled by a controller (not illustrated). The photographing unit may further a light source to brighten the inside of the sample S when an image is taken through the camera 300. Furthermore, the camera 300 may take an image of the inside of the space 111 through a laser shooting technique so as to reduce a decrease of light reflection in the space 111.

FIGS. 2 and 3 illustrate other examples of the above-described pressurizing member 130.

The pressurizing member 130' illustrated in FIG. 2 may include an integrated body 135, unlike the example illustrated in FIG. 1. The body 135 may be mounted to move upward and downward in the high-pressure cell 100. The body 135 may be formed of a transparent material, for example, a material containing quartz. Furthermore, like the example illustrated in FIG. 2, a camera 300 may be arranged to face the top surface of the body 135. The camera 300 may observe the surface of the sample S through the body 135.

The pressurizing member 130" illustrated in FIG. 3 may include a hollow body 136 and a transparent member 137. The hollow body 136 may be arranged to move upward and downward in the high-pressure cell 100 and a transparent member 137, and the transparent member 137 may be positioned in the internal space of the body 136 and formed of a transparent material, for example, a material containing quartz. Furthermore, like the example illustrated in FIG. 2, a camera 300 may be arranged above the transparent member 137 so as to face the top surface of the transparent member 137. The camera 300 may observe the surface of the sample S through the transparent member 137.

The protrusion 134 illustrated in FIG. 1 may be formed on the outer circumferential surfaces of the bodies 135 and 136 in the examples of FIGS. 2 and 3.

Hereafter, the process of the experiment apparatus having the above-described configuration will be described. First, the sample S may be stored in the space 111 of the first body 110 from which the second body 120 is removed, and the second body 120 and the pressurizing member 130,130', or 130" may be coupled to the top of the first body 110. Then, the pressurizing member 130,130', or 130" may be lowered to be contacted with the top surface of the sample S. During this process, the bottom of the recovery member 200 may be inserted into the sample S. Then, water may be supplied into the space 111 through the first supply path 112 at the bottom of the first body 110, and the sample S in the space 111 may be set to a temperature and pressure condition of 6 to 8° C. and 1500 to 2000 psi and then pressurized to a pressure corresponding to the pressure of an actual site (for example, up to 3 MPa) by the pressurizing member 130,130', or 130". The pressure may be increased in steps by the pressurization. During such an operation, the temperature, the pressure, and the vertical displacement of the sample S may be monitored in real time. When the pressurization to the required pressure is completed, dissociation of gas hydrate may be induced, and gas extracted through the dissociation may be recovered through the recovery member 200.

During the recovery process through the recovery member 200, the surface deformation of the sample S may be observed through the transparent region 130,130', or 130". The deformation of the sample S may be more precisely analyzed and stored as data through the camera 300.

According to the embodiment of the present invention, the experiment apparatus 1 may diversify the temperature and pressure condition applied to the sample S, the material forming the sample S, and the conditions related to the dissociation method and process and the recovery method for gas hydrate, and acquire information through which ground surface deformation in an actual site can be precisely estimated.

While the present invention has been described with respect to the specific embodiments, it will be apparent to those skilled in the art that various changes and modifications may be made without departing from the spirit and scope of the invention as defined in the following claims.

INDUSTRIAL APPLICABILITY

According to the embodiment of the present invention, surface deformation of a sample during gas hydrate recovery may be observed with the naked eye or a camera and then analyzed and stored as data, the temperature or pressure condition within the high-pressure cell may be set to various conditions similar to those of an actual site, and an experiment may be performed to acquire information through which a ground deformation rate in an actual site can be precisely estimated.

The invention claim is:

1. An experiment apparatus comprising:
   a high-pressure cell having a space in which a sample containing gas hydrate is stored
   a pressurizing body comprising:
   a hollow body mounted to move in one direction in the high-pressure cell;
   a first cap mounted at an opened end of the body; and
   a second cap mounted at the other opened end of the body so as to face the surface of the sample, and
   the first and second caps are formed of a transparent material, wherein the pressurizing body is mounted to move in one direction in the high-pressure cell, and configured to move to pressurize the sample stored in the space, wherein the surface of the sample is observable along the longitudinal direction of the pressurizing body through the pressurizing body from outside; and
   a recovery member including a flow path inserted into the sample so as to recover the gas hydrate contained in the sample to the outside.

2. The experiment apparatus according to claim 1, wherein the second cap is formed of a material containing quartz.

3. The experiment apparatus according to claim 1, wherein the surface of the pressurizing body, contacted with the surface of the sample through the movement of the pressurizing body, is formed with one surface of the second cap.

4. The experiment apparatus according to claim 1, further comprising a photographing unit including a camera, the photographing unit arranged to observe the surface of the sample through the first and second caps.

5. The experiment apparatus according to claim 1, wherein the pressurizing body comprises an integrated body mounted to move in one direction in the high-pressure cell, and the body is formed of a transparent material.

6. The experiment apparatus according to claim 5, wherein the body is formed of a material containing quartz.

7. The experiment apparatus according to claim 5, further comprising a photographing unit including a camera, the photographing unit arranged to observe the surface of the sample through the body.

8. The experiment apparatus according to claim 1, wherein the pressurizing unit comprises:
   a hollow body arranged to move in one direction in the high-pressure cell; and
   a transparent member positioned in the body and formed of a transparent material.

9. The experiment apparatus according to claim 8, wherein the transparent member is formed of a material containing quartz.

10. The experiment apparatus according to claim 8, further comprising a photographing unit including a camera, the photographing unit arranged to observe the surface of the sample through the transparent member.

* * * * *